United States Patent [19]

Rapoport et al.

[11] 4,045,440

[45] Aug. 30, 1977

[54] METHOD OF PRODUCING THEBAINE FROM CODEINE AND ORIPAVINE FROM MORPHINE

[75] Inventors: Henry Rapoport; Randy B. Barber, both of Berkeley, Calif.

[73] Assignee: The United States of America as represented by the Department of Health, Education and Welfare, Washington, D.C.

[21] Appl. No.: 724,018

[22] Filed: Sept. 16, 1976

[51] Int. Cl.² .............................................. C07D 489/02
[52] U.S. Cl. .................................................... 260/285
[58] Field of Search ........................................ 260/285

[56] References Cited

FOREIGN PATENT DOCUMENTS 1,133,392  7/1962  Germany

OTHER PUBLICATIONS

Barber et al., J. Med. Chem., vol. 18, No. 11, pp. 1074–1077 (Nov. 1975).
Martin et al., J. Org. Chem., vol. 33, 3758–3761 (1968).

*Primary Examiner*—Donald G. Daus
*Assistant Examiner*—Diana G. Rivers
*Attorney, Agent, or Firm*—John S. Roberts, Jr.; Norman J. Latker; Thomas G. Ferris

[57] ABSTRACT

A method of producing thebaine from codeine and oripavine from morphine which comprises (a) producing the 0-6 methyl ethers from codeine and morphine using potassium hydride and methyl iodide as the O-alkylation agents and (b) subsequently oxidizing the respective 0-6 methyl ethers of codeine and morphine to shift from allylic structure to a dienol ether structure using an oxidizing amount of $MnO_2$ in tetrahydrofuran to produce thebaine from codeine and oripavine from morphine. In the case of morphine, it is preferable to protect the 0-3 position by acetylation prior to the oxidizing step. Both the etherification and oxidizing steps are carried out under a protecting blanket such as nitrogen and the reactions are carried out preferably under atmospheric pressure and ambient temperature with the exception of the etherification affecting the 0-6 position which may be commenced by cooling with ice.

4 Claims, No Drawings

METHOD OF PRODUCING THEBAINE FROM CODEINE AND ORIPAVINE FROM MORPHINE

The present invention is concerned with producing particularly certain phenanthrene opiate derivatives and in particular thebaine and oripavine. It has been found that these members of the opium alkaloid family may be produced by the present process from the most abundant opium alkaloids, namely, morphine and codeine, and the production of thebaine and oripavine, which are quite rare in nature, has greater pharmacological potential for the production of drugs combatting addiction.

Essentially, the present process involves starting with codeine and morphine and producing the 0-6 methyl ether from each and further oxidizing the C-ring which contains the 0-6 substituent to oxidize or dehydrogenate and effect a shift from an allyl ether to a dienol ether. This results in the loss of 2 hydrogens from the ring C and the consequent change of $\Delta^{7,8}$ to $\Delta^{6,7}$ and $\Delta^{8,14}$.

In the case of morphine which, by this process, produces oripavine, it is preferred to block the 0-3 position of the C ring prior to oxidizing. This may be conveniently done by acetylation to produce the O-acetate, although the reaction will go without this protective step with reduced yield.

A preferred solvent or carrier in both the etherification procedure and the oxidation procedure with manganese dioxide is tetrahydrofuran, an acyclic ether. Satisfactory alternatives are ethyl ether and dioxane.

As illustrative, the structures for morphine and oripavine are set out below and Table 1 shows the structure relationships of the reactants and products of this invention.

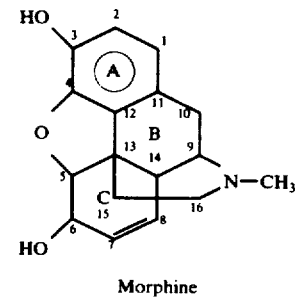

Morphine

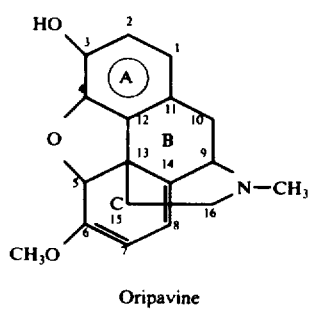

Oripavine

TABLE 1

Structures of Certain Opiates Chemically Related to Morphine

| Nonproprietary Name | Chemical Radicals and Positions | | | Other Changes+ |
|---|---|---|---|---|
| | 3* | 6* | 16* | |
| Morphine | —OH | —OH | —CH$_3$ | — |
| Oripavine | —OH | —OCH$_3$ | —CH$_3$ | (1) |

TABLE 1-continued

Structures of Certain Opiates Chemically Related to Morphine

| Nonproprietary Name | Chemical Radicals and Positions | | | Other Changes+ |
|---|---|---|---|---|
| | 3* | 6* | 16* | |
| Codeine | —OCH$_3$ | —OH | —CH$_3$ | — |
| Thebaine | —OCH$_3$ | —OCH$_3$ | —CH$_3$ | (1) |

*The numbers 3, 6, and 16 refer to positions in the morphine molecule as shown above.
+Other changes in the morphine molecule are:
(1) Double bonds at $\Delta^{6,7}$ and $\Delta^{8,14}$ replacing $\Delta^{7,8}$.

PRIOR ART

The prior art appears vacant as to the conversion of allylic ethers to dienol ethers using MnO$_2$ as an oxidant and specially in the application of the conversion of thebaine from codeine and oripavine from morphine. The present process utilizing codeine and morphine as reactants first produces an ether at the 0-6 position of the C ring using potassium hydride and methyl iodide, the latter as a methylating agent.

As a second step, the codeine methyl ether and the morphine 0-6 methyl ether (preferably as the 0-3 acetate) are then shaken with tetrahydrofuran and manganese dioxide resulting in thebaine and oripavine, respectively.

The basic journal article of the present inventors is herewith cited:

Barber and Rapoport, *J. Med. Chem.*, 18:1074–1076 (November 1975).

REACTANTS

The first step of the process is 0-alkylation at 0-6 of ring C of the phenanthrene structure utilizing potassium hydride and methyl iodide. In the case of morphine, the 0-3 position may be blocked by acetylation using acetic acid.

The second step is oxidation of the C ring with manganese dioxide. Of the various forms of manganese dioxide available, all will function as oxidizing agents and the investigators preferred the γ isomer, which is more prevalent (see Kirk-Othmer, *Encyclopedia of Chemical Technology* II, Vol. 13, pages 19–20). In the oxidation, the γ MnO$_2$ gave yields ranging from 67–82% overall and, in addition, MnO$_2$ on a charcoal support was utilized. The manganese dioxide gave significantly better yields than organic oxidizing agents, such as DDQ (2,3-dichloro-5,6-dicyano-1,4-benzoquinone) or o-chloranil. In a comparative reaction with DDQ producing thebaine, it was found that at least two equivalents of DDQ were necessary, the first equivalent forming a benzene insoluble complex with codeine methyl ether (CME). Of the inorganic oxidants CrO$_3$.PY$_2$ and selenium dioxide were also used but no production of thebaine from codeine methyl ether was detected.

The oxidation of the C ring with maganese dioxide produces an oxidation and change of the allylic ether to a dienol ether. This method may have broad applicability based on the oxidation and consequent loss of two hydrogens and the production of the two double bonds in the dienol pattern. However, in the specific field of opiates, it was shown that the attempted oxidation of isocodeine methyl ether (i-CME) and geranyl methyl ether was not successful and both were recovered unchanged. It is surmised that in the case of i-CME the reason may be steric in nature, since the hydrogens being removed are trans. Therefore, one must recognize that the present process is specific to certain structures such as the present 0-6 morphine and codeine ethers.

THE CHANGE IN THE C RING

The oxidation of the C ring removes two hydrogens and the double bond at $\Delta^{7,8}$ becomes two double bonds at $\Delta^{6,7}$ and $\Delta^{8,14}$. Thus, the 0-6 methyl ether for codeine and morphine shifts from an allyl configuration to a dienol configuration. The preferred oxidizing agent is $MnO_2$ and the investigators have preferred $\gamma$ $MnO_2$. The contrasting value to other organic and inorganic oxidizing agents has been set out above.

REACTION CONDITIONS

A. The Etherifying Step at 0-6

In the investigative procedure, the etherifying step is carried out at ambient temperature and pressure. A 3:1 molar ratio is preferred for codeine/methyl iodide. In the production of morphine-6-methyl ether, potassium hydride was used with the methyl iodide and the morphine was added in the cold (ice). The remainder of the reaction was carried out at room temperature (rt).

B. Oxidation of the C Ring

An inert atmosphere is preferred in the oxidation step and the investigators teach, for example, a nitrogen blanket. The reaction is carried out at room temperature and a large molar excess of $MnO_2$ has been utilized; for example, 1.00 mmol of codeine methyl ether reacted with 25 mmol of $\gamma$ $MnO_2$ added sequentially.

THE PRODUCTS

Of the products produced, thebaine, although itself of no medicinal value, is the key intermediate in the manufacture of a number of drugs of commerical importance, e.g., naloxone, naloxone analogs, oxycodone, percodan, and extremely potent analgesics used on large animals. Thus, an abundant supply of thebaine is assured by this conversion from the much more abundant morphine and codeine.

Furthermore, oripavine, which has not been thoroughly pharmacologically investigated, offers major manufacturing advantages for certain compounds in which the active form contains a 3-hydroxy group. By using a suitable oripavine derivative, containing a blocked 3-hydroxy group, conversion to the 3-hydroxy compound becomes an easy, high-yield reaction.

EXAMPLE 1

Codeine Methyl Ether

An excess of potassium hydride (300 mol %, 35% dispersion in oil) was washed with hexane (3 × 50 ml, distilled from $CaH_2$) and then suspended in THF (50 ml, distilled from $LiAlH_4$). With stirring under a nitrogen atmosphere, a solution of codeine (1.00 g, 2.33 mmol) in 50 ml of THF was added to the KH suspension over a period of 2 hours and stirred for an additional hour. Methyl iodide (0.43 ml, 6.66 mmol) was added to the mixture rapidly and the reaction was quenched after 90 sec. with 20 ml of 1 N $NaOC_2H_5$ in ethanol. Water (50 ml) was added and the solution evaporated to remove organic solvents. The resulting aqueous mixture was extracted with chloroform (4 × 50 ml), and the chloroform extracts were washed with a small portion of water, dried over $MgSO_4$, and evaporated to give a crude solid which was crystallized from ethanol to give 0.87 g (83%), mp 138°–139°, identical with an authentic sample of codeine methyl ether by TLC, GC, mass spectrum, and NMR.

EXAMPLE 2

Thebaine by Oxidation with $\gamma$-$MnO_2$

A solution of codeine methyl ether (343 mg, 1.00 mmol) in THF (10 ml, distilled from $LiAlH_4$) was shaken vigorously with $\gamma$-$MnO_2$ (440 mg, 5.0 mmol) under a nitrogen atmosphere at room temperature. Further portions of $\gamma$-$MnO_2$ (440 mg, 5.0 mmol) were added at intervals of 1, 3, 5, and 10 hr. After 24 hr. the black mixture was filtered through a fine sintered glass funnel, the residue was washed with THF (4 × 50 ml), and the washings were combined with the original filtrate and evaporated to give 207 mg of crude thebaine. The $MnO_2$ was then washed with methanol (4 × 30 ml) which yielded an additional 119 mg of crude thebaine. The two fractions were combined and crystallized from ethanol to give thebaine (251 mg, 80%) identical with an authentic sample by mp (191°–192°), TLC, GC, mass spectrum [m/e 311 (M+)], and NMR.

EXAMPLE 3

Thebaine by Oxidation with DDQ

To a stirred solution of codeine methyl ether (156 mg, 0.5 mmol) in 5 ml of benzene under a nitrogen atmosphere was added 2,3-dichloro-5,6-dicyano-1,4-benzoquinone (DDQ) (119 mg, 0.525 mmol) and the dark green precipitate (272 mg) which formed was collected by filtration. The filtrate yielded 7 mg of CME. When 50 mg of the precipitate was partitioned between chloroform and aqueous $NaHCO_3$, 28 mg of CME was recovered from the chloroform layer. The green precipitate (50 mg) was suspended in 5 ml of benzene and another portion of DDQ (22 mg, 0.097 mmol) was added and the mixture was boiled overnight. The precipitate (64 mg), now red brown, was collected by filtration and was partitioned between chloroform and aqueous $NaHCO_3$ to give in the $CHCl_3$ phase 26 mg of an oil which by TLC and GC contained CME and thebaine in a 1:1 ratio.

EXAMPLE 4

Morphine 6-Methyl Ether

Potassium hydride (57.0 g, 331 mmol, 27% dispersion in oil) was washed with dry hexane, suspended in THF (1000 ml, distilled from $LiAlH_4$), and cooled in an ice bath under a nitrogen atmosphere. A solution of morphine monohydrate (11.4 g, 37.5 mmol) in 1 liter of THF was added slowly, and the resulting white suspension was stirred for 6 hours and allowed to warm to room temperature. Methyl iodide (2.7 ml, 43.4 mmol) was added and an aliquot of the reaction was analyzed after 25 min. by GC; no morphine remained and only heterocodeine was present. The reaction was quenched by slowly adding water and cooling in an ice bath. The solution was neutralized to pH 7, the THF was evaporated, the pH of the solution was readjusted to 12.5, and it was extracted with chloroform to remove any phenolic methyl ether. The pH was then adjusted to 8.6 and the solution extracted with chloroform-2-propanol (3:1). This extract was evaporated to give a brown oil from which heterocodeine (9.44 g) was crystallized from ethyl acetate. The mother liquor was chromatographed on thin layer ($CHCl_3$—$CH_3OH$—$NH_4OH$, 3:1:1%) to give additional heterocodeine (0.82 g); total yield, 91.6%; mp 242°-243°; NMR δ2.5 (s,3 H), 3.5 (s,3 H), 4.9 (d,1 H, J=3 Hz), 5.5 (m,2 H), 6.5 (q,2 H, J=4 Hz); mass spectrum m/e 299 (M+).

EXAMPLE 5

Morphine 3-Acetate 6-Methyl Ether

Acetic anhydride (0.35 ml, 3.70 mmol) was added to a solution of heterocodeine (0.97 g, 3.25 mmol) in pyridine (7.5 ml, distilled from BaO) at room temperature and under a nitrogen atmosphere. After 2.5 hours the reaction was complete (TLC and GC) and it was quenched with ice and water (125 ml). The resulting aqueous solution was extracted with chloroform (4 × 100 ml), and the chloroform extracts were washed with water, dried over $Na_2SO_4$, and evaporated to give 1.08 g (97%) of heterocodeine 3-acetate: mp 133.5°-134.0° on crystallization from ethanol; NMR δ3.5 (6-$OCH_3$), 2.5 ($NCH_3$), 2.8 ($OCOCH_3$); mass spectrum m/e 341 (M+). Anal. ($C_{20}H_{23}NO_4$) C, H, N.

EXAMPLE 6

Oripavine 3-Acetate

Portions of γ-$MnO_2$ (5 × 440 mg, 5 × 5.0 mmol) were added to a solution of heterocodeine 3-acetate (341 mg, 1.0 mmol) in THF (50 ml, distilled from sodium benzoketyl) at intervals of 1, 2, 3, and 4 hours at room temperature with shaking. After a total of 24 hours of shaking, the reaction mixture was filtered and the precipitate was washed with fresh THF (4 × 50 ml) which was combined with the filtrate and evaporated to give a tan foam of 264 mg, homogeneous by TLC. The precipitate was then washed with methanol (4 × 50 ml) to give an additional 82 mg which contained a trace of 3,6-dimethyl ether. The two residues were combined and crystallized from ethanol to give oripavine 3-acetate in 88% yield; mp 173°; mass spectrum m/e 339 (M+); homogeneous by TLC. Anal. ($C_{20}H_{23}NO_4$) C, H, N.

EXAMPLE 7

Oripavine

Oripavine 3-acetate (224 mg, 0.67 mmol) was dissolved in methanol-water (4:1, 25 ml) and 2 N NaOH (2 ml) was added. Reaction was complete in less than 2 minutes (TLC), 14 ml of water was added, the pH was lowered to 8, and the methanol was evaporated. The resulting aqueous solution was adjusted to pH 8.9 and extracted with chloroform-2-propanol (3:1, 5 × 50 ml). The extracts were combined, washed with aqueous $NaHCO_3$ (saturated, 2 × 75 ml), dried over $Na_2SO_4$, and evaporated to give 184 mg (93%) of oripavine; homogeneous by TLC; mass spectrum m/e 297 (M+); mp 199°-200°; NMR, same as thebaine minus 3-$OCH_3$.

We claim:

1. A method of producing thebaine from codeine and oripavine from morphine which comprises (a) producing the 0-6 methyl ethers from codeine and morphine using potassium hydride and methyl iodide as the O-alkylation agents and (b) subsequently oxidizing the respective 0-6 methyl ethers of codeine and morphine to shift from an allylic structure to a dienol ether structure using an oxidizing amount of $MnO_2$ in tetrahydrofuran to produce thebaine from codeine and oripavine from morphine.

2. The method of claim 1 wherein codeine is the reactant which is thereafter 0-alkylated to produce codeine 0-6 methyl ether which is subsequently oxidized by $MnO_2$ to produce thebaine.

3. The method of claim 1 wherein morphine is the reactant which is 0-alkylated to produce morphine 0-6 methyl ether and which is subsequently oxidized by $MnO_2$ to produce oripavine.

4. The method of claim 1 wherein the phenolic hydroxyl of morphine at the 3-OH position is protected by acetylation prior to the oxidation with $MnO_2$ to produce oripavine.

* * * * *